United States Patent [19]

Kondo et al.

[11] 4,094,886

[45] June 13, 1978

[54] PROCESS FOR PRODUCING ALLYL ALCOHOL DERIVATIVES USEFUL IN PROSTAGLANDIN SYNTHESIS

[75] Inventors: Kiyosi Kondo, Yamato; Daiei Tunemoto, Sagamihara, both of Japan

[73] Assignee: (Zaidanhojin) Sagami Chemical Research Center, Tokyo, Japan

[21] Appl. No.: 767,165

[22] Filed: Feb. 9, 1977

[30] Foreign Application Priority Data

Mar. 1, 1976  Japan ................................. 51-21161
Mar. 4, 1976  Japan ................................. 51-22667

[51] Int. Cl.$^2$ ............................................. C07D 307/93
[52] U.S. Cl. ........................... 260/345.9 P; 260/346.22
[58] Field of Search .......... 260/346.22, 345.9, 346.2 R

[56] References Cited

U.S. PATENT DOCUMENTS 3,975,427   8/1976   Untch ............................. 260/468 D

OTHER PUBLICATIONS

Evans et al., Tet. Letters No. 16, pp. 1385–1388, (1973).

*Primary Examiner*—Henry R. Jiles
*Assistant Examiner*—Bernard Dentz
*Attorney, Agent, or Firm*—Oblon, Fisher, Spivak, McClelland & Maier

[57] ABSTRACT

A novel process for producing allyl alcohol derivatives having the formula

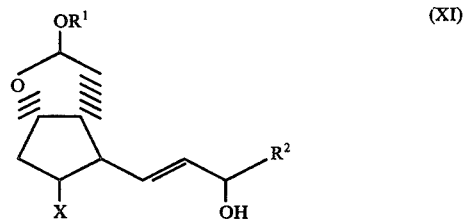

(XI)

wherein $R^1$ represents a hydrogen atom or a lower alkyl group; and $R^2$ represents an alkyl group which can have an inert substituent; and X represents a hydrogen atom, a hydroxy, an alkoxy, a tetrahydropyranyloxy or a silyloxy group; which are useful intermediates for the syntheses of prostaglandins and analogous compounds is disclosed. In the process, the allyl alcohol derivatives are produced starting from β-keto-esters and azides through a series of reactions.

3 Claims, No Drawings

PROCESS FOR PRODUCING ALLYL ALCOHOL DERIVATIVES USEFUL IN PROSTAGLANDIN SYNTHESIS

BACKGROUND OF THE INVENTION

1. Field of the Invention

The present invention relates to a novel process for producing allyl alcohol derivatives having the formula

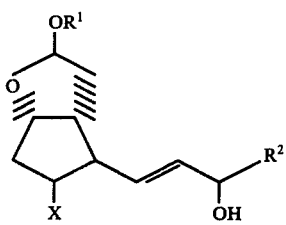
(XI)

wherein $R^1$ represents a hydrogen atom or a lower alkyl group, $R^2$ represents an alkyl group which can have an inert substitutent, and X represents a hydrogen atom, or a hydroxy, an alkoxy, a tetrahydropyranyloxy or a silyloxy group; which are novel compounds and are useful intermediates for the syntheses of prostaglandins and analogous compounds which have excellent physiological activities and are useful medicines.

2. Description of the Prior Art

Heretofore, various precursors for producing prostaglandins have been proposed. Various intermediates having lactone and lactol structures have been used and the syntheses of prostaglandins have been reported. [E. J. Corey et al., Tetrahedron Lett., 4753 (1971); R. B. Woodward et al., J. Amer. Chem. Soc., 95, 6853 (1973); E. J. Corey et al., J. Org. Chem., 40, 2265 (1975); E. J. Corey et al., J. Amer. Chem. Soc., 91, 5675 (1969); E. J. Corey et al., ibid., 93, 1490 (1971); P. Crabbe et al., Tetrahedron Lett., 115 (1975); E. J. Corey et al., ibid., 3091 (1973); D. Brewster et al., Chem. Commun., 1235 (1972); J. Fried et al., Tetrahedron Lett., 3899 (1973); J. Fried et al., J. Amer. Chem. Soc., 94, 4342, 4343 (1972); E. J. Corey et al., Tetrahedron Lett., 311 (1970); R. C. Kelly et al., J. Amer. Chem. Soc., 95, 2746 (1973)].

These precursors and processes have many advantages. However, they also have the following disadvantages; the starting materials are not easily obtained, selectivities of the reactions used are poor, expensive reagents are needed in some cases, the conditions of the reactions are not easily controlled, and the purification of the products is not easy. In particular alkyl groups residing at higher than position 14 of the prostanoic acid skeleton have been mostly introduced by Wittig condensation as shown by the references cited above, and the processes are thus not economical.

The inventors have investigated a novel route to prostaglandins and analogs which is operable in industrial processes and have found the process for producing allyl alcohol derivatives having the formula (XI) which can be easily converted to prostaglandins and analogs.

SUMMARY OF THE INVENTION

It is an object of the present invention to provide a process for producing allyl alcohol derivatives which are useful intermediates for the syntheses of prostaglandins and analogous compounds.

The object of the present invention has been attained by providing a process for producing an allyl alcohol derivative having the formula

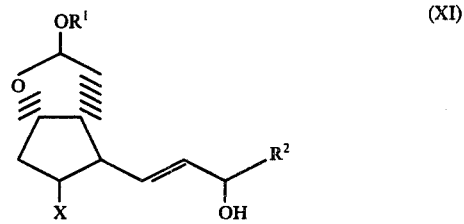
(XI)

wherein $R^1$ represents a hydrogen atom or a lower alkyl group, $R^2$ represents an alkyl group which can have an inert substituent, and X represents H, OH, alkoxy, tetrahydropyranyloxy, or silyloxy; which comprises treating a β-hydroxy-sulfoxide derivative having the formula

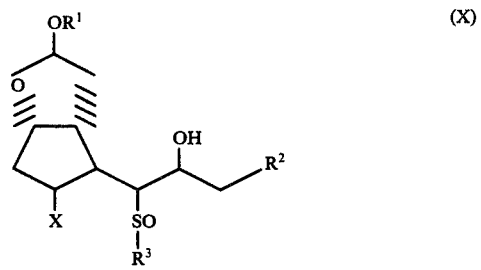
(X)

wherein $R^1$, $R^2$ and X are as defined above and $R^3$ is an aryl group which can have an inert substituent, with a base.

DETAILED DESCRIPTION OF THE PREFERRED EMBODIMENTS

The process of the present invention is summarized by the following reaction scheme.

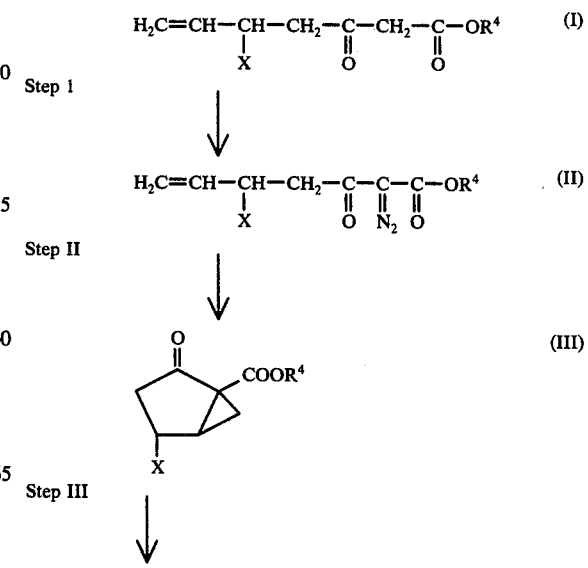

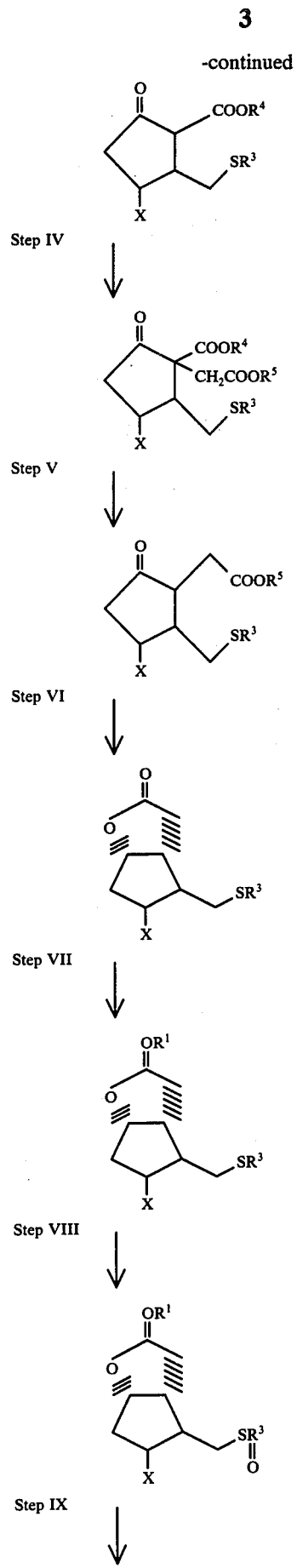

Step IV

Step V

Step VI

Step VII

Step VIII

Step IX

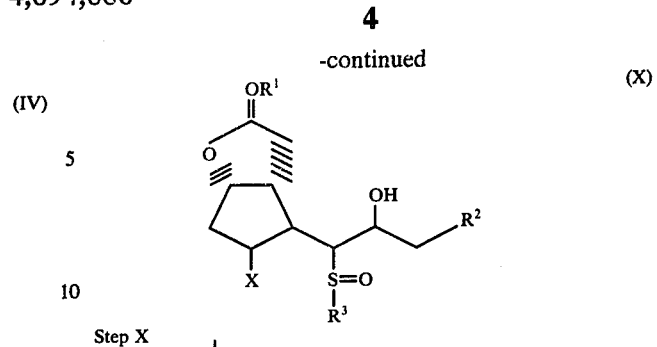

Step X

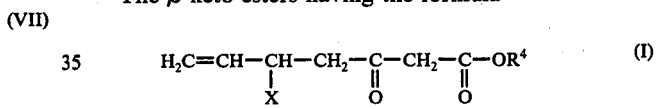

wherein $R^1$ represents a hydrogen atom or a lower alkyl group, especially a $C_1 - C_4$ alkyl group; $R^2$ represents an alkyl group especially a $C_3 - C_{10}$ alkyl group which can have an inert substituent; $R^3$ represents an aryl group which can have an inert substituent; $R^4$ represents an alkyl group; $R^5$ represents an alkyl group; and X represents a hydrogen atom, or a hydroxy, an alkoxy, a tetrahydropyranyloxy or a silyloxy group.

The β-keto-esters having the formula $$H_2C=CH-CH-CH_2-C-CH_2-C-OR^4 \quad (I)$$
$$\phantom{H_2C=CH-CH}|\phantom{-CH_2-}\|\phantom{-CH_2-}\|$$
$$\phantom{H_2C=CH-CH}X\phantom{-CH_2-}O\phantom{-CH_2-}O$$

which are the starting material in Step I, can easily be produced by the condensation or addition reaction of acetoacetic acid esters with the corresponding alkyl halides or carbonyl compounds.

Typical compounds having the formula (I) include β-keto-esters such as 3-oxo-6-heptenoic acid esters, 5-hydroxy-3-oxo-6-heptenoic acid esters, 5-benzyloxy-3-oxo-6-heptenoic acid esters, 3-oxo-5-(2'-tetrahydropyranyloxy)-6-heptenoic acid esters, 3-oxo-5-trimethylsilyloxy-6-heptenoic acid esters. Step I comprises a reaction of the β-keto-esters (I) with an azide.

Suitable azides include tosyl azide, benzenesulfonyl azide, phenyl azide, azidoformic acid esters and various other azides. The reaction of Step I should be conducted under basic conditions. Suitable such basic conditions can be attained by addition of alkali metal hydroxides such as sodium hydroxide and potassium hydroxide; alkali metal alkoxides such as sodium methoxide, sodium ethoxide, sodium t-butoxide, potassium t-butoxide; and organic amines such as triethylamine, tributylamine, dimethylaniline, pyridine and piperidine in the reaction system. The base is preferably added in an amount about equimolar to the starting materials.

In operation of the Step I, the reaction can be conducted without using a solvent. However, in order to increase the yield of the product under mild reaction conditions, it is preferable to use a solvent. Suitable solvents include acetonitrile, dimethylformamide, tetrahydrofuran, alcohols, ethers, methylene chloride and the like.

When the operation of Step I is conducted under the aforesaid conditions, the reaction can smoothly be performed without specific heating or cooling of the system to produce α-diazo-β-keto-esters.

Typical β-diazo-β-keto-esters having the formula (II)

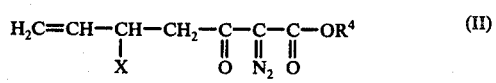

which are produced by the operation of Step (I) include α-diazo-β-keto-esters such as 3-oxo-2-diazo-6-heptenoic acid esters, 5-benzyloxy-2-diazo-3-oxo-6-heptenoic acid esters, 2-diazo-3-oxo-5-(2'-tetrahydropyranyloxy)-6-heptenoic acid esters, 2-diazo-3-oxo-5-trimethylsilyloxy-6-heptenoic acid esters.

In Step II, it is necessary to subject α-diazo-β-keto-esters having the formula (II) to conditions which enable the formation of a carbene or a carbenoid. The carbene or carbenoid forming condition can be attained by (1) treatment with a catalyst or (2) photoirradiation.

In the catalyzed decomposition method, a trace amount of catalyst such as metals or metal salts e.g. copper powder, copper bronze, copper halides, copper sulfate, copper acetylacetonate, copper-phosphine complex, silver oxide, silver nitrate and the like, is used in an inert atmosphere to form carbenoids. In the photodecomposition method, the compound (II) is directly irradiated or irradiated in an inert atmosphere to form carbenes. The conventional light sources used in photochemical industries such as a low pressure mercury lamp as well as high pressure mercury lamp can be used as the light source.

It is not always necessary to use a solvent in either the catalytic method or the photodecomposition method. However, in order to avoid the formation of by-products and to obtain the desired compound in high yield and selectivity, it is preferable to conduct the reaction in an inert medium. The inertness of the medium can be attained by conducting the reaction under an inert atmosphere, such as nitrogen or argon gas and using a solvent such as benzene, toluene, xylene, hexane, petroleum ether and the like, as the reaction medium.

In the Step III reaction, it is necessary to treat the bi-cyclo [3.1.0]-hexane-2-one derivative having the formula (III) with a mercaptan having the formula $R^3SH$ in the presence of a base. The base can be alkali metal hydroxides such as potassium hydroxide, sodium hydroxide; alkali metal alkoxides such as sodium methoxide, potassium methoxide, sodium ethoxide, potassium t-butoxide; and organic amines such as triethylamine, tributylamine, pyridine and the like.

The amount of base can range from a catalytic to an excess amount. However, it is preferable to use about equimolar amounts of base and starting material, so as to shorten the reaction time and to increase the yield. It is considered that the base used in Step III acts as a reagent for forming a mercaptide anion from the mercaptan $R^3SH$ in the reaction system.

In the operation of Step III, it is preferable to use a solvent. The solvents are preferably polar solvents which are inert to the reaction, such as alcohols, e.g. methanol, ethanol, t-butanol; ethers e.g. diethyl ether, tetrahydrofuran; dimethylformamide, acetonitrile, dimethyl sulfoxide and the like. It is also possible to attain the process of the invention by using a large excess of the mercaptans as a solvent. Under the above-mentioned conditions, the reaction can be smoothly conducted at the room temperature without any specific heating or cooling. The cyclopentanone compounds having an electron withdrawing substituent at the 2-position represented by the formula (IV)

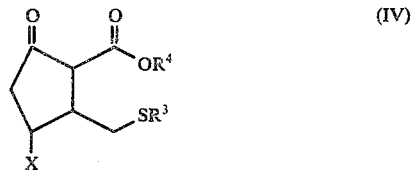

include 2-oxo-5-phenylthiomethyl-cyclopentanecarboxylic acid esters, 2-oxo-5-(p-tolylthiomethyl)-cyclopentanecarboxylic acid esters, 2-oxo-5-phenylthiomethyl-4-trimethylsilyloxy-cyclopentanecarboxylic acid esters, 2-oxo-5-phenylthiomethyl-4-(2'-tetrahydropyranyloxy)-cyclopentanecarboxylic acid esters, 4-benzyloxy-2-oxo-5-phenylthiomethylcyclopentanecarboxylic acid esters, 4-hydroxy-2-oxo-5-phenylthiomethylcyclopentanecarboxylic acid esters.

The cyclopentanone derivtives having an electron withdrawing substituent at the 2-position and a thiomethyl substituent at the 3-position which are produced by the process of the invention, have a variety of functionality which can easily be used for the introduction of the necessary substituents of prostanoids. The advantage of an electron withdrawing group at the 2-position is its strong and selective activation of the 2-position. Thus, it is easy to introduce various kinds of alkyl or alkenyl substituents at this position. Moreover, the activating group, i.e., the ester group, can easily be removed after the reaction. The advantage of a thiomethyl substituent at the 3-position is that, by the use of the activating effect of the arylthio group, the necessary side chain of the prostaglandins can be selectively introduced on the thiomethyl methylene.

In the Step IV reaction, the cyclopentanone carboxylic acid ester having the formula (IV) is converted to the cyclopentanone dicarboxylic acid ester having the formula (V) by reacting it with a lower alkyl haloacetic acid ester having the formula

wherein Y represents a halogen atom; in the presence of a base. Suitable bases include alkali metal carbonates e.g. potassium carbonate, sodium carbonate; alkali metal hydroxides e.g. potassium hydroxide, sodium hydroxide; alkali metal hydrides e.g. potassium hydride, sodium hydride; alkali metal alkoxides e.g. potassium methoxide, sodium methoxide, potassium ethoxide, sodium ethoxide, potassium t-butoxide; and organic amines e.g. triethylamine, tributylamine, pyridine, and the like.

In the Step V reaction, the cyclopentanone dicarboxylic acid ester having the formula (V) is converted to the cyclopentanone carboxylic acid ester having the formula (VI) by heating it in an alkali metal salt such as a halide of sodium, potassium or lithium or a hydrate thereof, or a cyanide of sodium, potassium or lithium, at 50° to 200° C.

It is also possible to convert (V) to (VI) by hydrolyzing the cyclopentanone dicarboxylic acid ester (V) in the presence of a base or an acid, and then, decarboxylating it by heating at 50° to 200° C, if desired, following by an esterification to obtain the cyclopentanone carboxylic acid ester (VI).

In the Step VI reaction, the carbonyl group in the cyclopentanone carboxylic acid ester having the formula (VI) is selectively reduced.

The typical cyclopentanone carboxylic acid esters include
2-(alkoxycarbonylmethyl)-3-phenylthiomethyl cyclopentanone,
2-(alkoxycarbonylmethyl)-3-(p-tolylthiomethyl) cyclopentanone,
2-(alkoxycarbonylmethyl)-4-hydroxy-3-phenylthiomethyl cyclopentanone,
2-(alkoxycarbonylmethyl)-3-phenylthiomethyl-4-(2'-tetrahydropyranyloxy)-cyclopentanone, 2-(alkoxycarbonylmethyl)-4-benzyloxy-3-phenylthiomethyl cyclopentanone, 2-(alkoxycarbonylmethyl)-3-phenylthiomethyl-4-trimethylsilyloxy cyclopentanone, and the like.

The reduction reaction can be accomplished by using a reducing agent, a catalytic reduction, or an electrolytic reduction.

Suitable reducing agent include complex metal hydrides such as lithium aluminum hydroxide, sodium borohydride and lithium borohydride. The reducing agent is used either in a stoichiometric amount or in excess.

In the catalytic reduction, suitable conventional catalysts for reduction include platinum oxide, nickel, copper chromite. The reduction can also be accomplished by nascent hydrogen which is formed by using zinc-hydrochloric acid (acetic acid), zinc-alkali metal hydroxide, sodium, aluminum, sodium amalgam, or aluminum amalgam in an aqueous medium.

It is preferable to use an inert solvent such as alcohols e.g. methanol, ethanol, t-butanol, and the like, or ethers e.g. diethyl ether, tetrahydrofuran, and the like.

In the post-treatment in order to dehydrate or dealcoholate, it is preferable to treat the reaction mixture with mineral acids such as sulfuric acid, hydrochloric acid, perchloric acid, and the like and acidic catalysts such as phosphoric acid, p-toluenesulfonic acid, trifluoromethanesulfonic acid, boron trifluoride etherate, and the like. The intermediate γ-hydroxy carboxylic acid or the ester thereof is converted to the object compound by the above-mentioned dehydration or dealcoholation procedures.

The reaction is smoothly performed at room temperature or higher temperature to obtain the object compound in high yield.

in the Step VII, Step VIII and Step IX reactions, β-hydroxysulfoxide derivatives are produced by reducing a lactone-sulfide having the formula (VII) to obtain the corresponding lactal sulfide and then reacting it with an alcohol having the formula R¹OH in the presence of an acidic catalyst to obtain the acetal-sulfide having the formula (VIII), and then oxidizing the acetal-sulfide to obtain the corresponding sulfoxide having the formula (IX), and reacting the sulfoxide with an aldehyde having the formula

R²CH₂COH in the presence of a strong base.

The lactone-sulfides used in the step VII reaction can be produced by the Step VI reaction.

The Step VII, Step VIII, and Step IX reactions include (a) a reduction, (b) an acetal formation, (c) an oxidation and (d) a condensation. These reactions are illustrated:

(a) Reduction

It is preferable to reduce the lactone-sulfide having the formula (VII) by using a reducing agent such as diisobutyl aluminum hydride, in an inert solvent such as ethers e.g. ethyl ether, tetrahydrofuran and aromatic hydrocarbons e.g. benzene, toluene, xylene.

The reaction temperature is preferably in a range of −100° C to 0° C. When it is higher than 0° C, the by-products which are formed by further reduction of the object lactol-sulfide would be produced.

(b) Acetal formation

The acetal formation is carried out by reacting the lactol-sulfide with an alcohol having the formula R¹OH in the presence of an acidic catalyst.

Typical acidic catalysts include mineral acids such as hydrochloric acid, sulfuric acid, phosphoric acid, and the like; organic acids such as p-toluenesulfonic acid, methanesulfonic acid, trifluoroacetic acid, and the like; or Lewis acids such as boron trifluoride etherate, zinc chloride, and the like. A catalytic amount of the acidic catalyst is sufficient.

Although an equimolar amount of the alcohol is sufficient to form an acetal from the lactol-sulfide, the alcohol can be used in large excess as solvent. Alternatively, the solvent used in the reduction step can be used. The reaction temperature is preferably in a range of −100° C to room temperature so as to prevent the formation of by-products. The acetal-sulfide having the formula (VIII) is obtained.

(c) Oxidation

In the oxidation, the acetal-sulfide having the formula (VIII) is oxidized with an oxidizing agent to produce the acetal-sulfoxide having the formula (IX).

Typical oxidizing agents include inorganic oxidizing agents such as hydrogen peroxide, oxygen, ozone, manganese dioxide, selenium dioxide, chromatic acid, nitric acid, dinitrogen tetraoxide, and the like; and organic oxidizing agents such as peracetic acid, perbenzoic acid, m-chloroperbenzoic acid, iodosobenzene, and the like.

In order to accomplish the oxidation without affecting the other reactive functional groups such as the acetal group of the starting material, it is preferable to use an organic peracid especially m-chloroperbenzoic acid. The amount of the oxidizing agent is usually an equimolar amount or an excess.

In the oxidation, it is preferable to use an inert solvent such as water; alcohols e.g. methanol, ethanol, and the like, ethers e.g. diethyl ether, tetrahydrofuran, dimethoxyethane, and the like; and acetic acid, chloroform, methylene chloride, benzene, and the like.

(d) Condensation

The reaction of the acetal-sulfoxide having the formula (IX) with the aldehyde having the formula R²CH₂CHO is carried out in the presence of a strong base.

Here, strong base means compounds having the capacity to form a carbon anion at the position adjacent to the sulfoxide. Typical such strong bases include lithium dialkylamides such as lithium diisopropylamide, alkyl lithiums such as n-butyl lithium, sec-butyl lithium, t-butyl lithium, and the like; and alkali metal hydrides such as sodium hydride, potassium hydride, and the like.

The condensation is preferably carried out by using the starting materials and the strong base in substantially equimolar amounts in an inert solvent such as ethers e.g. diethyl ether, tetrahydrofuran, diethoxyethane, and the like; dimethyl sulfoxide, hexamethylphosphoric triamide, and the like.

The condensation is smoothly performed at −50° C to room temperature to obtain the object β-hydroxy-sulfoxide having the formula (X).

In the Step X reaction, the allyl alcohol derivative having the formula (XI) is produced by treating the β-hydroxy-sulfoxide derivative having the formula (X) with a base.

Typical β-hydroxy-sulfoxide derivatives (X) include 6-(1'-benzenesulfinyl-2'-hydroxyoctyl)-3-methoxy-2-oxa-cis-bicyclo[3.3.0]octane, 3-methoxy-2-oxa-6-(1'-toluenesulfinyl-2'-hydroxyoctyl)-cis-bicyclo[3.3.0]octane, 6-(1'-benzenesulfinyl-2'-hydroxy-4'-methyl-octyl)-3-methoxy-2-oxa-cis-bicyclo[3.3.0]octane, 6-(1'-benzenesulfinyl-2'-hydroxy-7'-methyloctyl)-3-methoxy-2-oxa-cis-bicyclo[3.3.0]octane, 7-benzyloxy-3-methoxy-2-oxa-6-[1'-(p-toluene sulfinyl)-2'-hydroxyoctyl]-cis-bicyclo[3.3.0]octane, 6-(1'-benzenesulfinyl-2'-hydroxyoctyl)-3-methoxy-2-oxa-7-(2'-tetrahydropyranyloxy)-cis-bicyclo-[3.3.0]octane, 6-(1'-benzenesulfiny-2'-hydroxyoctyl)-3-methoxy-2-oxa-7-trimethylsilyloxy-cis-bicyclo[3.3.0]octane, 6-(1'-benzenesulfinyl-2'-hydroxyoctyl)-7-hydroxy-3-methoxy-2-oxa-cis-bicyclo[3.3.0]octane.

In the Step X reaction, the β-hydroxy-sulfoxide derivative (X) is treated with a base such as an alkali metal hydroxide e.g. sodium hydroxide, potassium hydroxide, and the like, alkali metal alkoxides e.g. sodium methoxide, sodium ethoxide, potassium methoxide, potassium t-butoxide, and the like or organic amines e.g. diethylamine, triethylamine, and the like.

A catalytic amount of the base is enough. It is possible to use a large amount of the base for accelerating the reaction.

Usually, it is preferable to use a thiophilic reagent with the base. For example, the yield can be increased by using simultaneously an alkali metal alkoxide and organic amine or a phosphorus compound such as trialkyl phosphite.

It is considered that the base acts as a catalyst for promoting the formation of a vinyl sulfoxide derivative by dehydration of the β-hydroxy-sulfoxide derivative (X) and the rearrangement of the vinyl sulfoxide to an allyl sulfoxide derivative as follows.

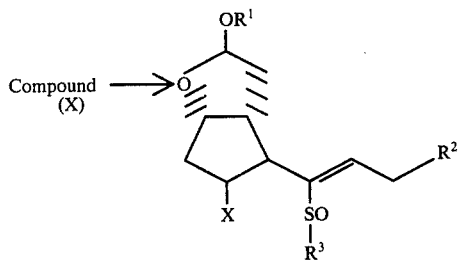

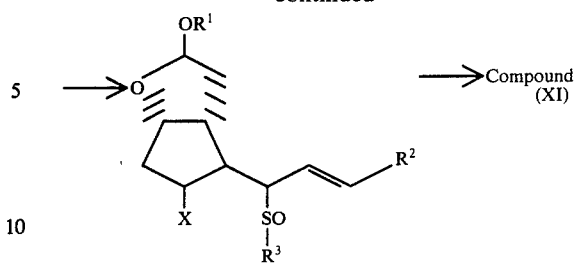

The conversion of the allyl sulfoxide derivative to the allyl alcohol derivative (XI) involves rearrangement and elimination of an aryl sulfinyl group. The reaction is promoted by using a thiophilic reagent.

In the reaction, it is preferably to use an inert solvent such as alcohols, e.g. methanol, ethanol, t-butanol, and the like, ethers e.g. diethyl ether, tetrahydrofuran and the like, dimethyl sulfoxide, hexamethylphosphoric triamide, and the like.

The reaction is smoothly performed at about 50° to 100° C.

Usually, it is preferable to carry out the reaction at the reflux temperature of each solvent for ease of operation.

Typical allyl alcohol derivatives (XI) include 6-(3'-hydroxy-trans-1'-octenyl)-3-methoxy-2-oxa-cis-bicyclo[3.3.0]octane, 6-(3'-hydroxy-trans-1'-butenyl) -3-methoxy-2-oxa-cis-bicyclo[3.3.0]octane, 3-hydroxy-6-(3'-hydroxy-trans-1'octenyl)-2-oxa-cis-bicyclo[3.3.0]octane, 7-benzyloxy-6-(3'-hydroxy-trans-1'-octenyl)-3-methoxy-2-oxa-cis-bicyclo[3.3.0]octane, 6-(3'-hydroxy-trans-1'-octenyl)-3-methoxy-2-oxa-7-(2'-tetrahydropyranyloxy)-cis-bicyclo[3.3.0]octane, 6-(3'-hydroxy-trans-1'-octenyl)-3-methoxy-2-oxa-7-trimethylsilyloxy-cis-bicyclo-[3.3.0]octane, 3,7-dihydroxy-6-(3'-hydroxy-trans-1'-octenyl)-2-oxa-cis-bicyclo[3.3.0-]octane. These allyl alcohol derivatives (XI) can be converted to prostaglandins and analogs according to the known procedures.

PREPARATION 1

A solution of p-toluenesulfonyl azide (592 mg; 3 mmol) in 1 ml of acetonitrile was added at room temperature to a solution of 3-oxo-6-heptenoic acid methyl ester (468 mg; 3 mmol) and triethylamine (306 mg; 3 mmol) in 5 ml of acetonitrile. The mixture was stirred for about 2 hours and the solvent was distilled off under a reduced pressure and the product was dissolved in 50 ml of ether. The solution was washed with a 5% aqueous solution of potassium hydroxide until no color remained in the aqueous phase and was further washed with a saturated aqueous solution of sodium chloride. The ether solution was dried over anhydrous magnesium sulfate and was filtered and condensed under a reduced pressure to obtain 530 mg of 2-diazo-3-oxo-6-heptenoic acid methyl ester as a yellow oily product. The crude product can be purified by distillation under reduced pressure.

Yield: 97%

Boiling point: 67° – 68° C/0.4 mmHg.

Infrared spectrum (cm$^{-1}$): 2120, 1725, 1655.

NMR spectrum (CCl$_4$) δ: 3.77 (s,3H), 4.65 – 5.20 (m, 2H), 5.47 – 6.13 (m, 1H)

PREPARATION 2

In an argon atmosphere, the unpurified 2-diazo-3-oxo-6-heptenoic acid methyl ester of Preparation 1 (4.55 g, 25 mmol) was dissolved in 100 ml of benzene. Anhydrous cupric sulfate (2.5 g) was added as a catalyst to the solution. The mixture was stirred for about 3 hours under reflux. After confirming the disappearance of the starting materials by thin layer chromatography, the reaction mixture was filtered through a Celite column. The solvvent was distilled off from the filtrate under reduced pressure and the remaining oily product was distilled under a reduced pressure to obtain 2.92 g of 2-oxo-bicyclo[3.1.0]hexane-1-carboxylic acid methyl ester as an oily product.

Yield: 69% based on methyl 3-oxo-6-heptenoate.
Boiling point: 90° C/0.7 mmHg.
NMR spectrum (CCl$_4$) δ: 1.33 (t, J=5Hz, 1H), 1.77 – 2.30 (m, 4H), 2.30 – 2.73 (m, 2H), 3.68 (s, 3H).
Mass spectrum m/e (%): 154 (55), 126 (87), 123 (56), 113 (94), 67 (62), 66(54), 59 (75).
Infrared spectrum (cm$^{-1}$): 1755, 1725.

PREPARATION 3

Thiophenol (660 mg: 6 mmol) was added to a solution of potassium t-butoxide (650 mg: 6 mmol) in 5 ml of t-butyl alcohol. The mixture was stirred for 10 minutes. A solution of 2-oxo-bicyclo[3.1.0]hexane-1-carboxylic acid methyl ester of Preparation 2(924 mg, 6 mmol) in 2 ml of t-butyl alcohol was added to the mixture. After stirring the mixture at room temperature for about 30 minutes, most of the solvent was distilled off under reduced pressure. Ether was added to the residue and dilute hydrochloric acid was added to acidify the solution, and the ethereal solution was washed with a saturated aqueous solution of sodium chloride and was dried over anhydrous magnesium sulfate and was filtered. The solvent was distilled off under reduced pressure. The remaining crystals were recrystallized from ether and n-hexane to obtain 2-oxo-5-phenylthiomethyl-cyclopentenecarboxylic acid methyl ester as white crystals.

Yield: 93%.
Melting point: 41° – 42° C.
Infrared spectrum (cm$^{-1}$): 1765, 1730, 1585, 1570, 1480, 1440, 1223, 1024, 740, 690.
NMR spectrum (CCl$_4$) δ: 1.37–2.67 (m, 5H), 2.70 – 3.50 (m, 3H), 3.68 (s, 3H), 7.03 – 7.65 (m, 5H).
Mass spectrum m/e (%): 264 (18), 141 (65), 123 (65), 110 (30), 109(100).

PREPARATION 4

2-Oxo-5-phenylthiomethyl cyclopentane carboxylic acid methyl ester (792 mg; 3 mmol) and ethyl bromoacetate (501 mg; 3 mmol) were dissolved in acetone (30 ml), and were admixed with potassium carbonate (415 mg; 3 mmol). The mixture was refluxed with stirring for 12 hours, and then was cooled to room temperature.

The precipitate was filtered and the solvent was distilled off under reduced pressure. The residue was purified by silica gel column chromatography to obtain 1-(ethoxycarbonylmethyl)-2-oxo-5-phenylthiomethyl cyclopentane carboxylic acid methyl ester (674 mg; 64%) as a viscous oily product.

The resulting 1-(ethoxycarbonylmethyl)-2-oxo-5-phenylthiomethylcyclopentane carboxylic acid methyl ester (640 mg; 1.83 mmol) was dissolved in dimethyl-formamide (20 ml) and was admixed with anhydrous lithium iodide (250 mg; 1.85 mmol). The mixture was refluxed with vigorous stirring for 5 hours and was cooled to room temperature. The reaction product was extracted by adding ether (50 ml) and dilute hydrochloric acid (50 ml) to the reaction mixture. The ether extract was washed with a saturated sodium chloride solution and was dried over anhydrous magnesium sulfate. The solution was filtered and the solvent was distilled off under reduced pressure. The residue was purified by silica gel column chromatography to obtain 2-(ethoxycarbonylmethyl)-3-phenylthiomethyl cyclopentanone (420 mg) as an oily product.

Yield: 78%.
Infrared spectrum (cm$^{-1}$); 1740, 1185, 740, 690.

PREPARATION 5

2-(Ethoxycarbonylmethyl)-3-phenylthiomethyl-cyclopentanone (480 mg; 1.65 mmol) was dissolved in methanol (10 ml) and was admixed with sodium borohydride (31 mg; 0.83 mmol). The mixture was stirred at room temperature for 30 minutes and was acidified with acetic acid (1 ml).

Most of the solvent was distilled off under reduced pressure. The reaction product was extracted by adding ether (50 ml) and an aqueous solution of ammonium chloride, and the ether extract was washed with a saturated aqueous sodium chloride solution and was dried over anhydrous magnesium sulfate. After filtration, the solvent was distilled off under reduced pressure. The residue (400 mg) was dissolved in benzene (20 ml) and was admixed with p-toluene-sulfonic acid (10 ml). The mixture was refluxed for two hours and the reaction mixture was cooled to room temperature and was washed with a dilute aqueous sodium bicarbonate solution and was post-treated by the conventional method. The residue was recrystallized from a mixture of ether and hexane to obtain 2-oxa-3-oxo-6-phenylthiomethyl cis-bicyclo[3.3.0]octane (310 mg) as white crystals.

Yield: 76%.
Melting point: 72° to 73° C.
Infrared spectrum (cm$^{-1}$): 1763, 1750, 1580, 1570, 1480, 1185, 740, 690.

PREPARATION 6

2-Oxa-3-oxo-6-phenylthiomethyl-cis-bicyclo[3.3.0]-octane (107 mg; 0.43 mmol) was dissolved in dry toluene (10 ml) and the solution was cooled at −75° C in an argon atmosphere. A solution of diisobutyl aluminum hydride in n-hexane (0.86 mmol) was slowly added dropwise from a syringe to the solution with stirring. The mixture was stirred for 3 hours at the same temperature and then, methanol was added to decompose it. Since the reaction mixture was in a gel form at room temperature, it was admixed with water and ethyl acetate.

The precipitate was filtered through Celite and the reaction product was twice extracted with ethyl acetate. The extract was washed with a saturated aqueous sodium chloride solution and was dried over anhydrous magnesium sulfate. After filtration, the filtrate was concentrated to yield a viscous oily residue. The residue was purified by silica gel column chromatography to obtain 97 mg of 3-hydroxy-2-oxa-6-phenylthiomethyl cis-bicyclo[3.3.0]octane as a viscous oily product.

Yield: 90%.
Infrared spectrum (cm$^{-1}$): 3400.

NMR spectrum (CDCl$_3$) δ: 1.03 – 3.12 (m, 10H), 3.30 – 4.12(br s, 1H), 4.35 – 4.96 (m, 1H), 5.33 – 5.60 (m, 1H), 6.97 – 7.48 (m, 5H).

PREPARATION 7

3-Hydroxy-2-oxa-6-phenylthiomethyl-cis-bicyclo[3.3.0]octane (94 mg, 0.38 mmol) was dissolved in methanol (10 ml). A methanol solution of a catalytical amount of boron trifluoride eterate in methanol (1 ml) was added to the solution in an argon atmosphere.

The mixture was stirred at −20° C for 1.5 hours and then at 0° C for 1 hour. After confirming the disappearance of the starting material by thin layer chromatography (ethyl acetate: n-hexane = 3 : 1), an aqueous solution of sodium bicarbonate was added to the mixture.

Most of methanol was distilled off under reduced pressure and the product was extracted with ethyl acetate. The extract was washed with a saturated aqueous sodium chloride solution and dried over anhydrous magnesium sulfate, and was filtered. The filtrate was concentrated and the residue was purified by silica gel column chromatography to obtain 84 mg of 3-methoxy-2-oxa-6-phenylthiomethyl cis-bicyclo[3.3.0]octane a viscous oily product.
Yield: 84%.
Infrared spectrum (cm$^{-1}$): 1200, 1100, 1055.
NMR spectrum (CCl$_4$): 1.10 – 2.98 (m, 10H), 3.18 (s, 3H), 4.27 – 4.90 (m, 1H), 4.93 (d, J=5Hz, 1H), 6.90 – 7.33 (m, 5H).

PREPARATION 8

3-Methoxy-2-oxa-6-phenylthiomethyl-cis-bicyclo[3.3.0]octane (82 mg; 0.31 mmol) was dissolved in methylene chloride (10 ml), and m-chloroperbenzoic acid (0.32 mmol) was added to the solution under cooling with water and the mixture was stirred for 3 hours. After confirming the disappearance of the starting material by thin layer chromatography (ethyl acetate: n-hexane = 3:1), ammonia gas was fed into the reaction mixture to precipitate the resulting ammonium m-chlorobenzoate. The precipitate was filtered through a Celite layer and the filtrate was washed with an aqueous solution of sodium thiosulfate. Ammonia gas was fed to confirm no further precipitation. The filtrate was further washed with water and dried over anhydrous magnesium sulfate and was further filtered. The filtrate was concentrated under reduced pressure. The residue was purified by silica gel column chromatography to obtain 80 mg of 6-benzenesulfinylmethyl-3-methoxy-2-oxa-cis-bicyclo[3.3.0]octane.
Yield: 92%.
Infrared spectrum (cm$^{-1}$); 1100, 1045.
NMR spectrum (CDCl$_3$): 1.13 – 3.10 (m, 10H), 3.30 (s, 3H), 4.38 – 4.93 (m, 1H), 5.03 (d, J=5Hz, 1H), 7.32 – 7.78 (m, 5H).

PREPARATION 9

In an argon atmosphere, diisopropylamine (650 mg; 6.45 mmol) was dissolved in tetrahydrofuran (20 ml) and the solution was cooled to −10° C. A hexane solution of n-butyl lithium (4.2 ml, 6.45 mmol) was added to the solution with stirring. After stirring the reaction mixture for 15 minutes, the reaction mixture was cooled to −75° C, and was admixed with a solution of 6-benzenesulfinylmethyl-3-methoxy-2-oxa-cis-bicyclo[3.3.0]-octane (1.8 g, 6.45 mmol) in tetrahydrofuran (hereinafter referring to as THF) (3 ml). The mixture was stirred at −75° C for 30 minutes and then, at 0° C for about 1 hour and then, was further cooled at −75° C and was admixed with a solution of n-heptylaldehyde (735 mg, 6.45 mmol) in THF (3 ml). The mixture was kept at −75° C for about 1 hour and then was gradually heated and was stirred at 0° C for 5 hours. The reaction product was decomposed with an aqueous solution of ammonium chloride and was extracted with ethyl acetate. The extract was washed with a saturated aqueous sodium chloride solution and was dried over anhydrous magnesium sulfate, and was filtered. The filtrate was concentrated under reduced pressure. The residue was purified by silica gel column chromatography to obtain 1.97 g of 6-(1'-benzenesulfinyl-2'-hydroxyoctyl)-3-methoxy-2-oxa-cis-bicyclo[3.3.0]octane as a viscous oily product.
Yield: 78%.
Infrared spectrum (cm$^{-1}$): 3400, 1045.

PREPARATION 10

In accordance with the process of Preparation 9, propionaldehyde (116 mg, 2 mmol) was added to the solution of carbanion prepared by using 6-benzenesulfinylmethyl-3-methoxy-2-oxa-cis-bicyclo[3.3.0]octane (560 mg, 2 mmol) to obtain 560 mg of 6-(1'-benzenesulfinyl-2'-hydroxy-butyl)-3-methoxy-2-oxa-cis-bicyclo[3.3.0]octane as a viscous oily product.
Yield: 72%.
Infrared spectrum (cm$^{-1}$): 3400, 1040.

PREPARATION 11

6-(1'-Benzenesulfinyl-2'-hydroxy-octyl)-3-methoxy-2-oxa-cis-bicyclo[3.3.0]octane (1.5 g; 3.73 mmol) was dissolved in t-butyl alcohol (20 ml) and was admixed with potassium t-butoxide (560 mg; 5 mmol) and diethylamine (365 mg; 5 mmol) and the mixture was refluxed for one night.

After confirming the disappearance of the starting material by thin layer chromatography, the reaction mixture was cooled to room temperature, and admixed with an aqueous solution of ammonium chloride and the reaction product was extracted with ethyl acetate. The extract was washed with a saturated aqueous sodium chloride solution and was dried over anhydrous magnesium sulfate. After filtration, the filtrate was concentrated under reduced pressure and the residue was purified by silica gel column chromatography (ethyl acetate: n-hexane =1 : 4) to obtain 530 mg of 6-(3'-hydroxy-trans-1'-octenyl)-3-methoxy-2-oxa-cis-bicyclo[3.3.0]octane as a viscous oily product.
Yield: 53%.
Infrared spectrum (cm$^{-1}$): 3400, 1100, 970.
NMR spectrum (CDCl$_3$) δ: 0.87 (t, J=6Hz, 3H), 1.04–2.70 (m, 16H), 3.26(s, 3H), 3.98(d, J=6Hz, 1H), 4.52(t, J=6Hz, 1H), 5.01(d, J=5Hz, 1H), 5.45 (two dd, J=16Hz, J=6Hz, 2H).

PREPARATION 12

6-(3'-Hydroxy-trans-1'-octenyl)-3-methoxy-2-oxa-cis-bicyclo[3.3.0]octane (100 mg, 0.37 mmol) was dissolved in a mixture of acetonitrile and water (2 : 1, 9 ml) and several drops of 0.03N-HCl was added to the solution. The solution was stirred at room temperature for 3 hours. Most of the acetonitrile was distilled off and the reaction product was extracted with ether, and the extract was post-treated by washing, drying and concentrating in the conventional method. The residue was purified by silica gel column chromatography (ethyl acetate : n-hexane = 1: 1) to obtain 74 mg of 3-hydroxy- 6-(3'-hydroxy-trans-1'-octenyl)-2-oxa-cis-bicyclo[3.3.0]-octane as a viscous oily product.
Yield: 78%
Infrared spectrum (cm$^{-1}$): 3400, 1060, 1010, 970.
NMR spectrum (CDCl$_3$) δ: 0.87(t, J=6Hz, 3H), 1.08-2.86(m, 16H), 3.98(dd, J=6Hz, 1H), 4.67(t, J=6Hz, 1H), 5.47(two dd, J=16Hz, J=6Hz, 2H).

PREPARATION 13

In an argon atmosphere dimysyl sodium solution was prepared from sodium hydride (810 mg with oil 16.8 mmol) and dimethyl sulfoxide (10 ml). The solution was slowly added dropwise to a dimethyl sulfoxide solution (20 ml) of 4-carboxybutyltriphenylphosphonium bromide (3.6g, 8.4 mmol) at room temperature in an argon atmosphere to obtain a red brown solution. After about 15 minutes, a solution of 3-hydroxy-6-(3'-hydroxy-trans-1'-octenyl)2-oxa-cis-bicyclo[3.3.0]octane (533 mg, 2.1 mmol) in dimethyl sulfoxide (3 ml) was added to the resulting solution. The mixture was stirred at room temperature for 3 hours. An aqueous solution of potassium hydroxide was added to the reaction mixture and the mixture was washed three times with methylene chloride.

The aqueous phase was acidified with hydrochloric acid and the reaction product was twice extracted with methylene chloride. The methylene chloride solution was combined and washed with water and was dried over anhydrous magnesium sulfate. The solvent was distilled off under reduced pressure. The residual mixture was purified by silica gel column chromatography (ethyl acetate: n-hexane = 1 : 1) to obtain 580 mg of 9α-hydroxy-15-hydroxy-cis-5-trans-13-prostadienoic acid (11-deoxyprostaglandin F$_{2α}$) which was a mixture of 15-epimers.
Yield: 82%.
Infrared spectrum (cm$^{-1}$): 3400, 1710, 970.
NMR spectrum (CDCl$_3$)δ: 0.89 (t, J=5Hz, 3H), 1.10 - 3.50 (m, 22H), 4.27 (m, 2H), 5.46 (m,4H), 6.63 (br s, 1H).

PREPARATION 14

In accordance with the process of Preparation 11, 6-(1'-benzenesulfinyl-2'-hydroxy-butyl)-3-methoxy-2-oxa-cis-bicyclo[3.3.0]octane (1.0 g, 3 mmol), potassium t-butoxide (560 mg, 5 mmol) and diethylamine (365 mg, 5 mmol) were used as the starting materials to obtain 340 mg of 6-(3'-hydroxy-trans-1'-butenyl)-3-methoxy-2-oxa-cis-bicyclo[3.3.0]octane as an oily product.
Yield: 60%.
Infrared spectrum (cm$^{-1}$): 3400, 1100, 970.

PREPARATION 15

In an argon atmosphere, a 50% sodium hydride dispersion in mineral oil (960 mg; 20 mmol) was suspended with 50 ml of dried tetrahydrofuran. A solution of methyl acetoacetate (2.32 g; 20 mmol) in 5 ml of THF was added to said suspension with stirring. After 10 minutes, a solution of n-butyl lithium (20 mmol) in n-hexane was added dropwise to the mixture.

After the addition, the mixture was further stirred at a temperature of about 0° C for 30 minutes. The reaction mixture was cooled to −40° C, and then a solution of acrolein (1.12 g; 20 mmol) in 5 ml of THF was added dropwise to the reaction mixture. After the addition, the mixture was further stirred at this temperature for about 4 hours. The mixture was gradually warmed to room temperature and most of the solvent was distilled off under reduced pressure. The concentrated reaction mixture was treated with dilute hydrochloric acid and then with ether. The aqueous layer was extracted with ether. The ether solution was washed with a saturated aqueous solution of sodium chloride and dried over anhydrous magnesium sulfate. The solution was filtered and then the solvent was distilled off under reduced pressure. The residue was distilled under reduced pressure to obtain 2.25 g of 5-hydroxy-3-oxo-6-heptenoic acid methyl ester.
Yield: 65 %.
Boiling point: 105° - 107° C/1.0 mmHg;
Infrared spectrum (cm$^{-1}$); 1745; 1715, 1645;
Nuclear magnetic resonance (NMR) spectrum (CCl$_4$)δ:
2.66 (ABX, J$_{AX}$= 6.5, J$_{BX}$= 5.5 Hz 2H), 3.33 (broad s, 1H) 3.43 (s, 2H), 3.68 (s, 3H9, 4.48(m, 1H), 4.94 - 5.35(m, 2H), 5.64 - 6.02(m, 1H).

PREPARATION 16

To a solution of 5-hydroxy-3-oxo-6-heptenoic acid methyl ester (2.18 g; 12.7 mmol) in 50 ml of dry ether, was added dihydropyran (2.18 g; 12.7 mmol) and a catalytic amount of p-toluenesulfonic acid with stirring and cooling in a water bath.

The mixture was stirred overnight at room temperature. An aqueous solution of sodium bicarbonate was added to the reaction mixture, the product was extracted with ether and was treated by the conventional method to obtain a viscous oily product. The product was purified by silica gel column chromatography (ethyl acetate: n-hexane = 1.5 : 8.5) to obtain 2.7 g of 3-oxo-5-(2'-tetrahydropyranyloxy)-6-heptenoic acid methyl ester as an oil.
Yield: 76 %.
Infrared spectrum (cm$^{-1}$): 1750, 1720, 1655, 1625, 1020,
NMR spectrum (CCl$_4$)δ:
1.24 - 1.98 (m, 6H), 2.21 - 3.02 (m, 2H), 3.20 - 3.98 (m, 2H), 3.43 (s, 2H), 3.70 (s, 3H), 4.38 - 4.75 (m, 2H), 4.87 - 6.20 (m, 3H).

PREPARATION 17

In accordance with the process of Preparation 15, a dianion solution of methyl acetoacetate (20 mmol) was produced. The solution was cooled to −40° C. A solution of acrolein (1.12 g; 20 mmol) in 5 ml of THF was added to the solution with stirring. The mixture was stirred at −40° C for 30 minutes and was warmed to 0° C over 1 hour and then was cooled to −40° C again.

To the mixture was added with stirring a solution of benzyl bromide (3.08 g; 18 mmol) in 6 ml of a mixture of THF:HMPA = 1:1 and the resulting mixture was kept at −10° overnight.

The reaction mixture was treated by the conventional method and the oily product was purified by silica gel column chromatography with a solvent of ethyl acetate and n-hexane (1 : 9) to obtain 1.1 g of 5-benzyloxy-3-oxo-6-heptenoic acid methyl ester.
Yield: 23 %. based on benzyl bromide:
Infrared spectrum (cm$^{-1}$) : 1750, 1720, 1655, 1630;
NMR spectrum (CCl$_4$)δ: 2.13 - 3.17 (m, 2H), 3.31 (s, 2H), 3.63 (s, 3H), 3.93 - 4.67 (m, 3H), 4.97 - 6.06 (m, 3H), 6.93 - 7.44 (m, 5H).

PREPARATION 18

To an ice-cooled solution of the 5-hydroxy-3-oxo-6-heptanoic acid methyl ester (344 mg, 2mmol) of Preparation 15 and trimethylsilyl chloride (217 mg; 2mmol) in 25 ml of dried ether was added dropwise a solution of triethylamine (202 mg, 2 mmol) in 3 ml of dried ether. The mixture was stirred overnight at room temperature and was poured into a saturated aqueous solution of sodium chloride and the product was extracted with ether.

The ether extract was dried over anhydrous magnesium sulfate. After filtering, the solvent was distilled off under reduced pressure and the residue was purified by silica gel column chromatography to obtain 360 mg of 3-oxo-5-trimethylsilyloxy-6-heptenoic acid methyl ester as an oily product.
Yield: 74%.
Infrared spectrum (cm$^{-1}$); 1750, 1720, 1650, 1630
NMR spectrum (CCl$_4$)δ: 0.07 (s, 9H), 2.10 – 3.00 (m, 2H), 3.33 (s, 2H), 3.69 (s, 3H), 4.32 – 4.77 (m, 1H), 4.86 – 6.10 (m, 3H).

PREPARATION 19

In accordance with the process of Preparation 1, 3-oxo-5-(2'-tetrahydropyranyloxy)-6-heptenoic acid methyl ester (1.84 g; 7.3 mmol), triethylamine (0.75 g; 7.5 mmol) and p-toluenesulfonyl azide (1.46 g; 7.4 mmol) were used as starting materials to obtain 1.79 g of 2-diazo-3-oxo-5-(2'-tertrahydropyranyloxy)-6-heptenoic acid methyl ester as a yellow viscous oily product.
Yield: 88%.
Infrared spectrum (cm$^{-1}$): 2125, 1725, 1655;
NMR spectrum (CCl$_4$)δ: 1.27 – 1.93 (m, 6H), 2.65 – 3.32 (m, 2H), 3.45 – 4.10 (m, 2H), 3.79 (s, 3H), 4.40 – 4.78 (m, 2H), 4.90 – 6.22 (m, 3H).

PREPARATION 20

In accordance with the process of Preparation 1, 5-benzyloxy-3-oxo-heptenoic acid methyl ester (1.07 g; 4.1 mmol), p-toluene-sulfonyl azide (810 mg; 4.1 mmol) and triethylamine (450 mg; 4.5 mmol) were used as starting materials to obtain 1.16 g of 5-benzyloxy-2-diazo-3-oxo-6-heptenoic acid methyl ester as a yellow oily product.
Yield: 98 %,
Infrared spectrum (cm$^{-1}$); 2125, 1725, 1655,
NMR spectrum (CCl$_4$)δ: 2.57 – 3.53 (m, 2H), 3.72 (s, 3H), 4.03 – 4.60 (m, 3H), 4.98 – 6.11 (m, 3H), 7.12 (broad s, 5H).

PREPARATION 21

In accordance with the process of Preparation 1, 3-oxo-5-trimethylsilyloxy-6-heptenoic acid methyl ester (360 mg; 1.47 mmol), p-toluenesulfonyl azide (290 mg; 1.47 mmol) and triethylamine (150 mg; 1.47 mmol) were used as starting materials to obtain 330 mg of 2-diazo-3-oxo-5-trimethylsilyloxy-6-heptenoic acid methyl ester as a yellow oily product.
Yield: 84 %,
Infrared spectrum (cm$^{-1}$); 2120, 1725, 1655,
NMR spectrum (CCl$_4$)δ: 0.07 (s, 9H), 2.90 (ABX,$J_{AB}$ = 16; $J_{AX}$ = 8, $J_{BX}$ = 5 Hz, 2H, 3.78 (s, 3H), 4.40 – 4.78 (m, 1H), 4.93 – 6.01 (m, 3H).

PREPARATION 22

In 30 ml of anhydrous xylene, 2-diazo-3-oxo-5-(2'-tetrahydropyranyloxy)-6-heptenoic acid methyl ester (1.05 g; 3.8 mmol) was dissolved. A copper acetylacetone complex (100 mg) was added to the solution and the mixture was heated for 3 hours while refluxing. After distilling off most of the xylene under a reduced pressure, 30 ml of ether was added to the residue.

The precipitate formed was filtered and the filtrate was concentrated under reduced pressure. The residue was purified by silica gel column chromatography with a mixture of ethyl acetate and n-hexane (3 : 7) to obtain 500 mg of two types of isomers of 2-oxo-4-(2'-tetrahydropyranyloxy)-bicyclo[3.1.0]hexane-1-carboxylic acid methyl ester as a viscous oily product.
Yield: 52 %,
Isomer obtained from the first fraction.
Infrared spectrum (cm$^{-1}$): 1765, 1740, NMR spectrum (CCl$_4$)δ: 1.15 – 3.08 (m, 11H), 3.21 – 3.98 (m, 2H), 3.67 (s, 3H), 4.41 – 4.92 (m, 2H), Isomer obtained from the second fraction.
Infrared spectrum (cm$^{-1}$); 1765, 1740;
NMR spectrum (CCl$_4$)δ: 1.10 – 3.12 (m, 10H), 1.29 (t, J=5 Hz, 1H), 3.21 – 4.13 (m, 2H), 3.69 (s, 3H), 4.14 – 4.40 (m, 1H), 4.63 – 4.92 (m, 1H).

PREPARATION 23

In accordance with the process of Preparation 22, 5-benzyloxy-2-diazo-3-oxo-6-heptenoic acid methyl ester (1.16 g; 4 mmol) and copper acetylacetone complex (100 mg) were dissolved in 30 ml of anhydrous xylene. The reaction product was purified by silica gel column chromatography to obtain two types of isomers of 4-benzyloxy-2-oxo-bicyclo[3.1.0]hexane-1-carboxylic acid methyl ester (248mg) as an oily product.
Yield: 25 %,
Isomer obtained from the first fraction.
Infrared spectrum (cm$^{-1}$); 1765, 1745;
NMR spectrum (CCl$_4$)δ: 1.61 (t, J=5 Hz), 1.65 – 2.90 (m, 4H), 3.67 (s, 3H), 4.10 – 4.52 (m, 1H), 4.50 (s, 2H), 7.22 (broad s, 5H).
Isomer obtained from the second fraction.
Infrared spectrum (cm$^{-1}$): 1765, 1740;
NMR spectrum (CCl$_4$)δ: 1.10 (t, J=5 Hz), 1.67 – 2.86 (m, 4H), 3.73 (s, 3H), 3.92 – 4.25 (m, 1H), 4.53 (s, 2H), 7.24 (broad s, 5H).

PREPARATION 24

In accordance with the process of Preparation 22, 2-diazo-3-oxo-5-trimethylsilyloxy-6-heptenoic acid methyl ester (2.63 g; 9.7 mmol) and copper acetylacetone complex (200 mg) were dissolved in 20 ml of anhydrous benzene. The reaction product was purified by silica gel column chromatography to obtain two types of isomers of 2-oxo-4-trimethylsilyloxy-bicyclo[3.1.0]-hexane-1-carboxylic acid methyl ester (1.05 g).
Yield: 45 %,
Infrared spectrum (cm$^{-1}$): 1765, 1745.

PREPARATION 25

In accordance with the process of Preparation 3, potassium t-butoxide (246 mg; 2.2 mmol), thiophenol (220 mg; 2 mmol) and 2-oxo-4-trimethylsilyloxy-bicyclo[3.1.0]hexane-1-carboxylic acid methyl ester (484 mg; 2 mmol) were used to obtain 470 mg of 2-oxo-5-phenylthiomethyl-4-trimethylsilyloxy-cyclopentanecarboxylic acid methyl ester as a viscous oil.
Yield: 67 %,
Infrared spectrum (cm$^{-1}$); 1765, 1730, 1665, 1620.

What is claimed as new and desired to be secured by Letters Patent of the United States is:

1. A process fo producing an allyl alcohol derivative having the formula

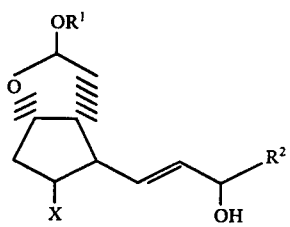

(XI), which comprises treating a β-hydroxysulfoxide derivative having the formula

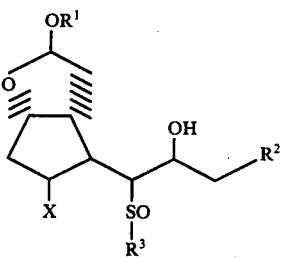

(X), with a base; wherein $R^1$ represents H or lower alkyl, $R^2$ represents an alkyl group which can have an inert substituent, $R^3$ represents an aryl group which can have an inert substituent, and X represents H, OH, alkoxy, tetrahydropyranyloxy, or a silyloxy group.

2. The process of claim 1, wherein said β-hydroxysulfoxide derivative (X) is produced by reacting a sulfoxide derivative having the formula

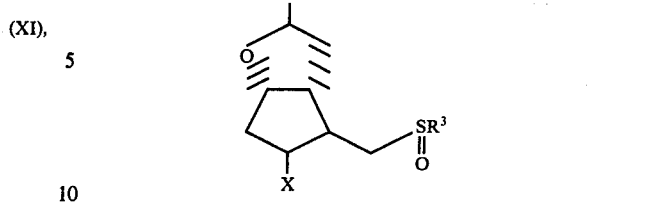

(IX), with an aldehyde having the formula $R^2CH_2CHO$ in the presence of a strong base; wherein $R^1$, $R^2$, $R^3$ and X are as defined in claim 1.

3. The process of claim 2, wherein said sulfoxide derivative (IX) is produced by:
reducing a lactone-sulfide having the formula

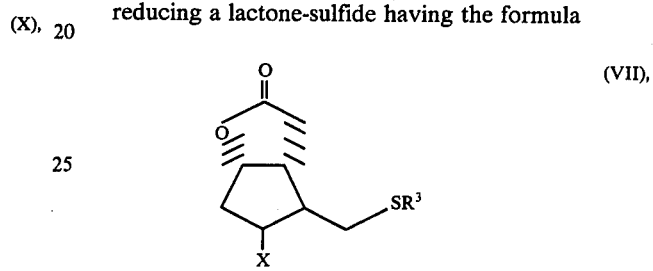

(VII), to produce a lactol-sulfide;
reacting said lactol-sulfide with an alcohol having the formula $R^1OH$ in the presence of an acidic catalyst to produce an acetal-sulfide; and
oxidizing said acetal-sulfide to produce said sulfoxide derivative (IX);
wherein $R^1$ represents H or lower alkyl, $R^3$ represents an aryl group which can have an inert substituent, and X represents H, OH, alkoxy, tetrahydropyranyloxy, or a silyloxy group.

* * * * *